United States Patent
Celebi et al.

(10) Patent No.: US 9,993,358 B2
(45) Date of Patent: *Jun. 12, 2018

(54) ROTATABLE PROSTHETIC ADAPTER

(71) Applicant: Medex International, Inc., Bethesda, MD (US)

(72) Inventors: Dogan Celebi, Burtonsville, MD (US); Hadiye Pinar Celebi, Burtonsville, MD (US)

(73) Assignee: MEDEX INTERNATIONAL, INC.

( * ) Notice: Subject to any disclaimer, the term of this patent is extended or adjusted under 35 U.S.C. 154(b) by 133 days.

This patent is subject to a terminal disclaimer.

(21) Appl. No.: 14/955,558

(22) Filed: Dec. 1, 2015

(65) Prior Publication Data

US 2016/0074182 A1 Mar. 17, 2016

Related U.S. Application Data

(63) Continuation of application No. 12/839,276, filed on Jul. 19, 2010, now Pat. No. 9,198,778.
(Continued)

(51) Int. Cl.
*A61F 2/76* (2006.01)
*A61F 2/78* (2006.01)
(Continued)

(52) U.S. Cl.
CPC .................. *A61F 2/80* (2013.01); *A61F 2/76* (2013.01); *A61F 2/78* (2013.01); *A61F 2/60* (2013.01);
(Continued)

(58) Field of Classification Search
CPC ...... A61F 2/60; A61F 2/76; A61F 2/78; A61F 2/80; A61F 2002/7875
See application file for complete search history.

(56) References Cited

U.S. PATENT DOCUMENTS 3,461,464 A   8/1969   Lindgren
4,157,722 A   6/1979   Hosono et al.
(Continued)

FOREIGN PATENT DOCUMENTS

FR   2410998 A1 *  7/1979   ............... A61F 2/76
GB   2087727 A  *  6/1982   ............... A61F 2/54
(Continued)

*Primary Examiner* — Marcia Watkins
(74) *Attorney, Agent, or Firm* — The Belles Group, P.C.

(57) ABSTRACT

The present invention is directed to a prosthetic adapter that allows for rotation of a prosthetic about a central axis. In one embodiment, the invention is a prosthetic adapter comprising: a first component comprising: a first pyramid block receiver comprising a first pyramid block receiving cavity; a collar integrally formed as a single monolithic component with the first pyramid block receiver, the collar comprising an inner surface forming a central cavity formed about a first central axis; and a second component comprising: a second pyramid block receiver comprising a second pyramid block receiving cavity; and a hub integrally formed as a single monolithic component with the second pyramid block receiver, the hub extending along a second central axis, the hub positioned in the central cavity so that the first and second central axes are substantially coaxial.

20 Claims, 11 Drawing Sheets

Related U.S. Application Data

(60) Provisional application No. 61/226,426, filed on Jul. 17, 2009.

(51) Int. Cl.
*A61F 2/80* (2006.01)
*A61F 2/60* (2006.01)
*A61F 2/50* (2006.01)

(52) U.S. Cl.
CPC .............. *A61F 2002/5016* (2013.01); *A61F 2002/5084* (2013.01); *A61F 2002/7875* (2013.01)

(56) References Cited

U.S. PATENT DOCUMENTS

| | | |
|---|---|---|
| 5,047,063 A | 9/1991 | Chen |
| 5,137,535 A | 8/1992 | Keller |
| D336,519 S | 3/1993 | Greene et al. |
| 5,226,918 A | 7/1993 | Silagy et al. |
| 5,507,837 A | 4/1996 | Laghi |
| 5,728,170 A | 3/1998 | Becker et al. |
| 5,888,214 A | 3/1999 | Ochoa |
| 5,888,233 A | 3/1999 | Randstroem |
| 5,888,234 A | 3/1999 | Littig |
| 5,957,615 A | 9/1999 | Orain |
| 5,980,573 A | 11/1999 | Shaffner |
| 6,361,569 B1 | 3/2002 | Slemker et al. |
| 6,398,817 B1 | 6/2002 | Hellberg et al. |
| 6,458,163 B1 | 10/2002 | Slemker et al. |
| 6,482,238 B1 | 11/2002 | Grundei |
| 6,689,171 B2 | 2/2004 | Slemker et al. |
| 6,994,732 B2 | 2/2006 | Stainbarger et al. |
| 7,101,403 B2 | 9/2006 | Chen |
| 2005/0209697 A1 | 9/2005 | Paponneau et al. |
| 2006/0049019 A1 | 3/2006 | Mosler et al. |
| 2006/0173554 A1 | 8/2006 | Slemker et al. |
| 2009/0082869 A1 | 3/2009 | Slemker |
| 2009/0292366 A1 | 11/2009 | Plowman |
| 2010/0036506 A1 | 2/2010 | Wang |

FOREIGN PATENT DOCUMENTS

| | | | |
|---|---|---|---|
| WO | 9840036 | 9/1998 | |
| WO | WO 03096940 A1 * | 11/2003 | ............... A61F 2/60 |

* cited by examiner

ROTATABLE PROSTHETIC ADAPTER

CROSS-REFERENCE TO RELATED PATENT APPLICATIONS

The present application is a continuation of U.S. patent application Ser. No. 12/839,276, filed Jul. 19, 2010, now U.S. Pat. No. 9,198,778, issued Dec. 1, 2015, which claims the benefit of U.S. Provisional Patent Application Ser. No. 61/226,426, filed Jul. 17, 2009, the entireties of which are hereby incorporated by reference.

FIELD OF THE INVENTION

This invention relates generally to adapters for coupling a prosthesis to a residual limb, and specifically to a prosthetic adapter that allows for rotation of the prosthesis about a central axis without uncoupling the prosthesis from the residual limb.

BACKGROUND

Various types of foot and leg prosthetic devices are well known in the art. Such devices frequently include some form of attachment for coupling the device to the distal end of the residual limb of an amputee and for extending to the ground to provide body support. One form of prosthesis is fabricated as an assembly having a flexible roll-on suction suspension liner, a socket, a shuttle lock, a lower leg component and a foot. The shuttle lock provides rigid attachment of the suspension liner to the socket and lower leg component while providing an easy way of enabling the amputee to release a prosthesis or other lower leg component from the amputee's residual limb. Other types of adaptors, such as a double head adaptor or a pyramid adaptor, are used to accommodate various situations such as when distance, or the length of the residual limb, is a problem.

Some currently available shuttle lock components utilized in below-knee prosthesis designs consist of a ratchet style or clutch style cylindrical body portion having a hole for receipt of the clutch pin, which is typically connected to the suspension liner. The body includes a clutch mechanism to disengage a gear located within the cylindrical body from the clutch pin. A problem with existing types of shuttle lock designs is that the cylindrical body must become integral and permanently molded to the prosthetic socket during fabrication. If the cylindrical body is improperly positioned during fabrication, the pin may not align easily and consistently with the shuttle lock latching mechanism. The only alternative is either to refabricate the socket, which can be time consuming and generate additional costs, or try to train the patient to overcome the difficulty he faces in donning the prosthesis. An example of an existing shuttle lock is disclosed in U.S. Pat. No. 5,888,234, issued Mar. 30, 1999 to Littig, the entirety of which is hereby incorporated by reference.

Consequently, there exists a need for a new and improved prosthetic adaptor for a prosthesis that can be positioned and repositioned at any time on the distal socket to provide on-axis alignment of the adaptor and hence, the prosthetic device, to alleviate patient frustration and eliminate rejection of an improperly aligned socket.

SUMMARY

The present invention is directed to a prosthetic adaptor that provides for rotation that enables an amputee to place a prosthesis into proper axial alignment without removing the entire prosthetic device from the amputee's residual limb.

In one aspect, the invention can be a prosthetic adapter comprising: a first component adapted to be coupled to a residual limb; a second component adapted to be coupled to a prosthesis, the first and second components adapted to be repetitively coupled and separated from one another; the first component or the second component comprising a collar having an outer surface and an inner surface, the inner surface forming a central cavity about a first central axis; the other one of the first component or the second component comprising a body portion and a cylindrical hub extending from the body portion along a second central axis, the cylindrical hub positioned in the central cavity so that the first and second central axes are substantially coaxial; and an anti-rotation member adjustable between: (1) a first state in which the anti-rotation member does not obstruct the cylindrical hub from being translated along the first central axis out of the central cavity; (2) a second state in which the anti-rotation member prohibits the cylindrical hub from being translated along the first central axis out of the central cavity while allowing the cylindrical hub to rotate within the central cavity of the collar about the first central axis; and (3) a third state in which the anti-rotation member prohibits the cylindrical hub from being translated along the first central axis out of the central cavity of the collar and prohibits rotation of the cylindrical hub within the central cavity of the collar about the first central axis.

In another aspect, the invention can be a prosthetic adapter comprising: a first component adapted to be coupled to a residual limb; a second component adapted to be coupled to a prosthesis; the first component or the second component comprising a collar having an outer surface and an inner surface, the inner surface forming a central cavity about a first central axis; the other one of the first component or the second component comprising a body portion and a hub extending from the body portion along a second central axis, the hub having a flange extending transversely from the hub, the flange spaced from the body portion so that a groove is formed between the body portion and the flange; the flange having a circular transverse cross-sectional profile having a first diameter, the inner surface of the collar having a circular transverse cross-sectional profile having a second diameter, wherein the first and second diameters are substantially equal, the hub positioned in the central cavity so that the first and second central axes are substantially coaxial; and an element extending through the collar and adjustable between: (1) a retracted state in which the element does not protrude from the inner surface of the collar; and (2) an anti-rotation state in which a tip portion of the element extends into the annular groove and engages a floor of the annular groove.

In yet another aspect, the invention can be a prosthetic adapter comprising: a first component adapted to be coupled to a residual limb; a second component adapted to be coupled to a prosthesis, the first and second components adapted to be repetitively coupled and separated from one another; the first component or the second component comprising a collar having an outer surface and an inner surface, the inner surface forming a central cavity formed about a first central axis; the other one of the first component or the second component comprising a body portion and a hub extending from the body portion along a second central axis, the hub positioned in the central cavity so that the first and second central axes are substantially coaxial; wherein when the hub is positioned within the central cavity of the collar, the hub has only two degrees of freedom, a first of the two degrees of freedom being rotation about the first central axis, and a second degree of the two degrees freedom being translation along the first central axis.

In still another aspect, the invention can be a prosthetic adapter comprising: a first component adapted to be coupled to a residual limb; a second component adapted to be coupled to a prosthesis, the first and second components adapted to be repetitively coupled to and separated from one another; the first component comprising an upper portion and a lower portion, the upper portion of the first component comprising a first pyramid block receiver comprising a first pyramid block receiving cavity, the lower portion of the first component comprising a collar having an outer surface and an inner surface, the inner surface forming a central cavity about a first central axis, the first pyramid block receiver extending from a top of the collar and integrally formed therewith; the second component comprising an upper portion and a lower portion, the lower portion of the second component comprising a second pyramid receiver comprising a second pyramid block receiving cavity, the upper portion of the second component comprising a cylindrical hub extending from the second pyramid receiver along a second central axis and integrally formed therewith, the cylindrical hub positioned in the central cavity so that the first and second central axes are substantially coaxial; wherein when the cylindrical hub is positioned within the central cavity of the collar, the hub has only two degrees of freedom, a first of the two degrees of freedom being rotation about the first central axis, and a second of the two degrees of freedom being translation along the first central axis; and an anti-rotation member adjustable between: (1) a first state in which the anti-rotation member does not obstruct the cylindrical hub from being translated along the first central axis out of the central cavity; (2) a second state in which the anti-rotation member prohibits the cylindrical hub from being translated along the first central axis out of the central cavity while allowing the cylindrical hub to rotate within the central cavity of the collar about the first central axis; and (3) a third state in which the anti-rotation member prohibits the cylindrical hub from being translated along the first central axis out of the central cavity of the collar and prohibits rotation of the cylindrical hub within the central cavity of the collar about the first central axis.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE DRAWINGS

Figure 1:
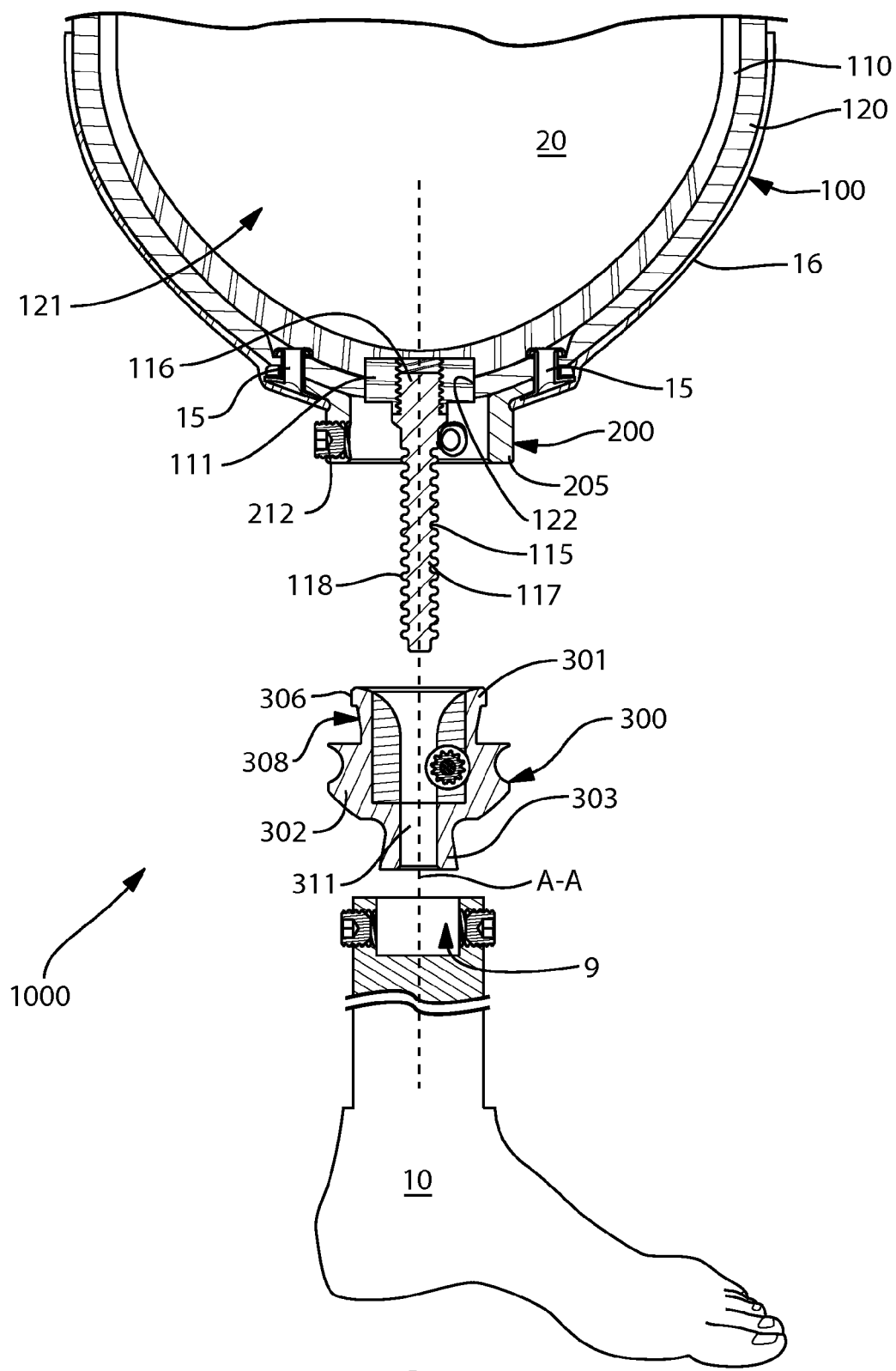
FIG. 1 is a cross-sectional schematic of a rotatable prosthetic adapter according to one embodiment of the present invention coupling a prosthetic foot to a residual limb.
Figure 2:
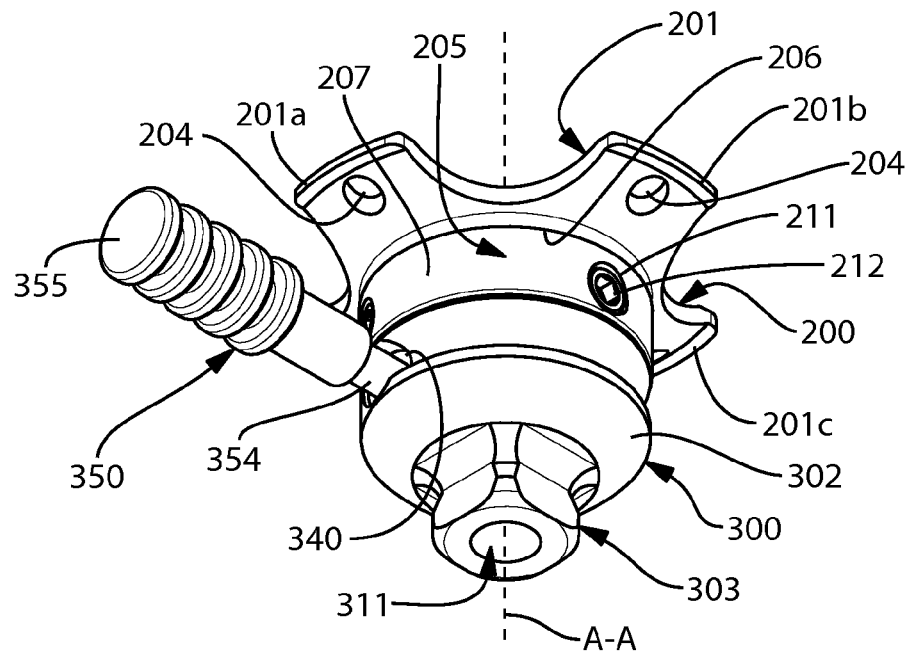
FIG. 2 is a bottom perspective view of the collar component and the hub component of the rotatable prosthetic of FIG. 1 in an assembled state.

Referring first to FIG. 1, a rotatable prosthetic adapter 1000 according to one embodiment of the present invention is illustrated. The rotatable prosthetic adapter 1000 is illustrated in a disassembled state wherein its components are arranged in axial alignment along longitudinal axis A-A for assembly and the coupling of a prosthetic foot 10 to a residual limb 20. While the rotatable prosthetic adapter 1000 is exemplified as being used to attach a prosthetic foot 10 to the residual limb 10, it is to be understood that the invention is in no way limited by the type of prosthesis used. Moreover, based on the disclosure of the present application, those skilled in the art will appreciate that the inventive concepts discussed herein can be incorporated into a wide variety of prosthetic adapter types.

The rotatable prosthetic adapter 1000 generally comprises a sleeve assembly 100, a collar component 200, and a hub component 300. In the illustrated embodiment, the hub component 300 is of the shuttle lock design. The sleeve assembly 100 comprises a flexible liner 110 and socket 120. The flexible liner 110 is a closed-end sleeve that fits snugly over the residual limb 20. The flexible liner 110 is preferably constructed of a gel, elastomeric, or other soft material to provide a cushioning layer for the residual limb 20. A clutch pin 115 is fixed to the flexible liner 110 and extends from the distal end of the residual limb 20 along the longitudinal axis A-A.

The clutch pin 115 is an elongated cylindrical structure comprising a threaded portion 116 and a serrated portion 117. The threaded portion 116 comprises helical threads that are used to secure the clutch pin 115 to a nut 111 that is embedded within the flexible liner 110. Of course, the clutch pin 115 can be fixed to the flexible liner by a wide variety of techniques that are known to those skilled in the art. The serrated portion 117 comprises a plurality of axially spaced ring-like serrations 118 for operably engaging a gear 352 of the clutch mechanism 350 of the hub component 300 (discussed in greater below). Of course, the exact structure of the clutch pin 115 can take on a wide variety of embodiments, none of which are to be considered limiting of the present invention.

The socket 120 is a rigid (or semi-rigid) sleeve structure that fits over the flexible liner 110. The socket 120 forms an internal receiving cavity 121 in which at least a portion of the residual limb 20 of the user nests. The socket 120 is preferably constructed of a material, such as carbon fiber, rigid plastics, or lightweight materials having sufficient rigidity and structural integrity. Of course, other materials can be used to construct the socket 120 and are know to those skilled in the art. The socket 120 (i.e., the internal receiving cavity 121) is preferably designed to be specific to the size and shape of the user's residual limb 20 to maximize comfort and the ability to control the prosthesis 10. The socket 120 further comprises an opening 122 at the distal end of the residual limb 20 through which the clutch pin 115 extends.

Figure 3:
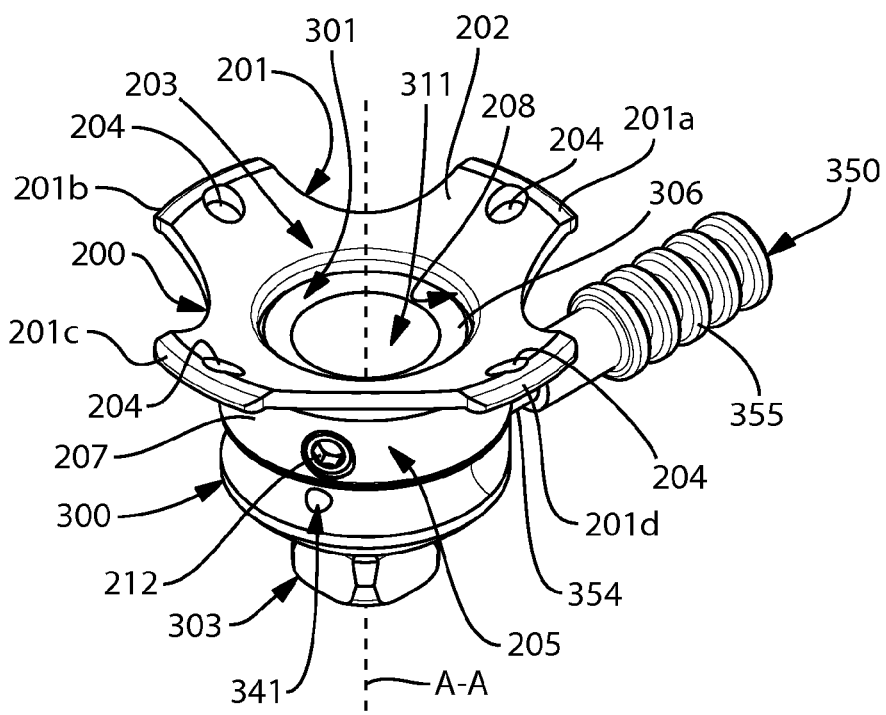
FIG. 3 is a top perspective view of the assembled collar component and hub component of FIG. 2.
Figure 4:
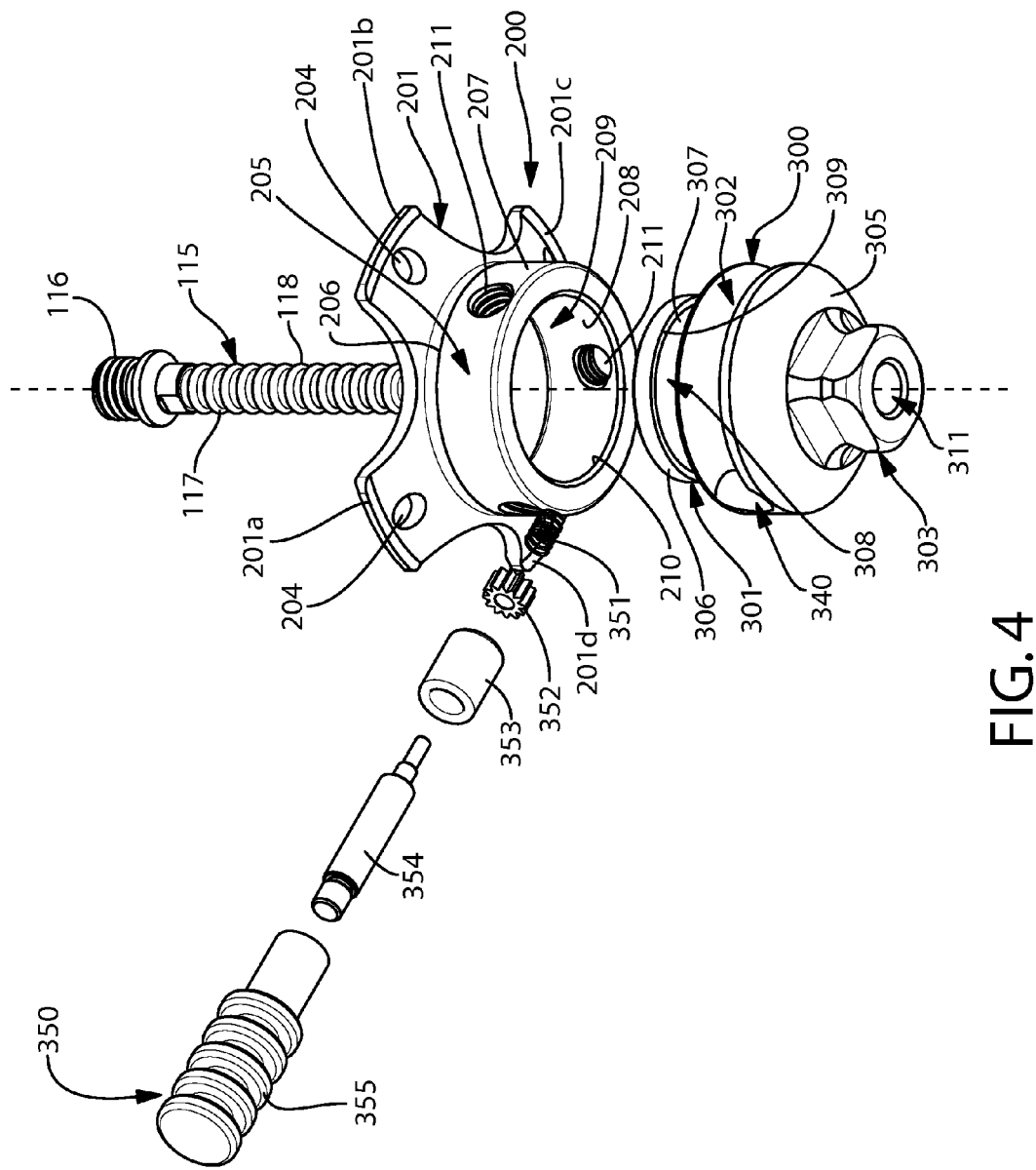
FIG. 4 is a bottom perspective view of the collar component and hub component of FIG. 2 in an exploded state, with the addition of a clutch pin.
Figure 5:
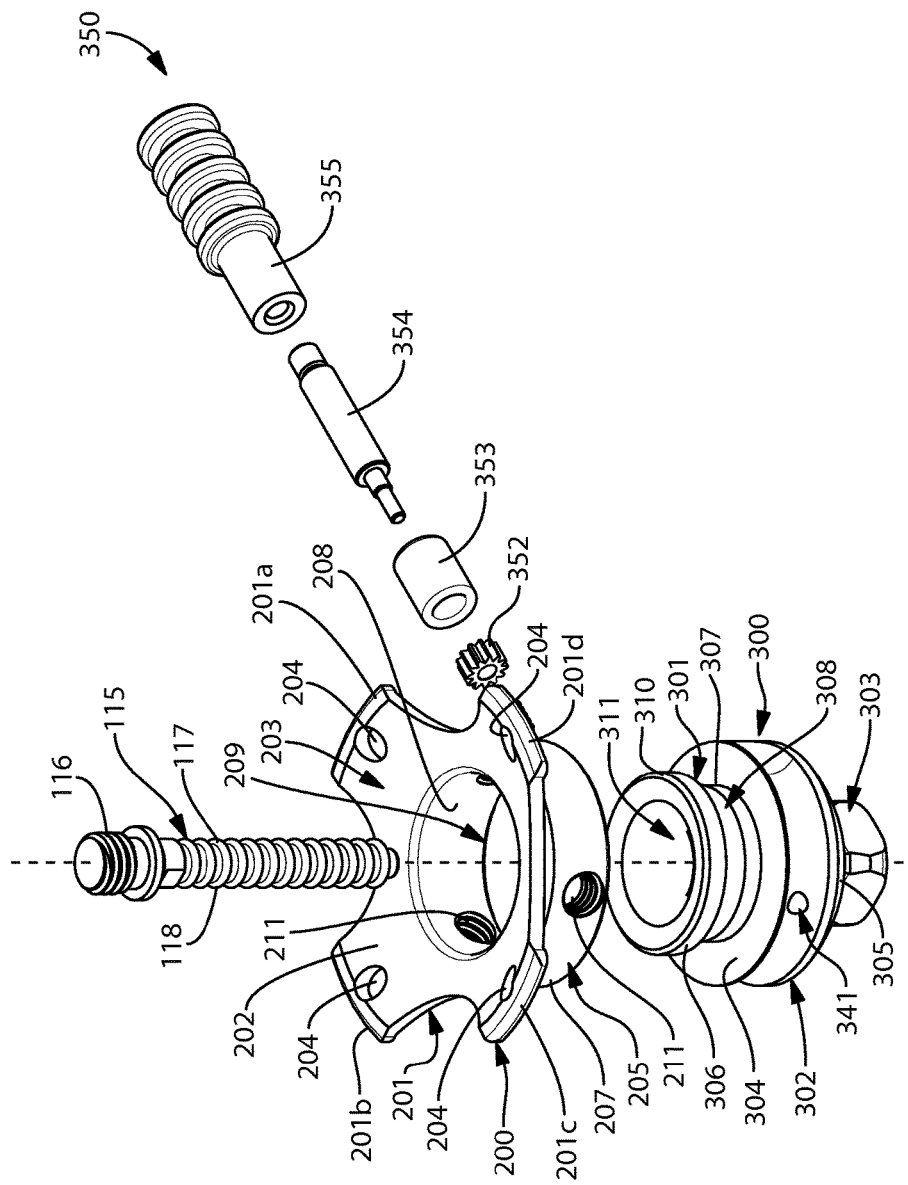
FIG. 5 is a top perspective view of the collar component and hub component of FIG. 2 in an exploded state, with the addition of a clutch pin.

Referring to FIGS. 1 and 3, the collar component 200 is fixed to the sleeve assembly 100. More specifically, the collar component 200 is fixed to the socket 120 of the sleeve assembly 100 through a combination of fasteners 15 and a laminate 16. Suitable fasters 15 include without limitation rivets, nails, screws, bolts, and/or clamps. Any number of fasteners 15 can be used in conjunction with, or instead of, the laminate 16. Similarly, any number of laminates 16 can also be used in conjunction with, or instead of, the fasteners 15. Moreover, it is also possible to use other techniques to fix the collar component 200 to the socket 120, including without limitation, adhesives, thermal bonds, welding, chemical bonds, clamps, mechanical interference connections and/or combinations thereof. Furthermore, it is also contemplated that the collar component 200 could be integrally formed with the socket 120 if desired. Such an integral construction is within the scope of the present invention, unless specifically stated otherwise.

To assist with the fixing (and relative positioning) of the collar component 200 to the socket 120, the collar component 200 comprises a cup-shaped flange 201. The cup-shaped flange 201 has an upper concave surface 202 that forms a cup-shaped depression (or cavity) 203. The cup-shaped depression 203 provides a nesting volume in which the distal-most portion of the socket 120 can be positioned.

The cup-shaped flange 201 is an annular flange that circumferentially surrounds and extends laterally from the longitudinal axis A-A. It should be noted at this point that, for purposes of simplification in this detailed description, the reference axis A-A is interchangeable with both the first central axis I-I (FIG. 6) of the collar component 200 and the second central axis II-II (FIG. 6) of the hub component 300. The longitudinal axis A-A is used for reference purposes when the first central axis I-I of the collar component 200 and the second central axis II-II are coaxial. However, in certain instances, the distinction between the first and second central axes I-I and II-II (FIG. 6) must be made because, when the collar component 200 and the hub component 300 are not assembled, it is possible to rotate one or both of the components 200, 300 so that the first and second central axes I-I and II-II (FIG. 6) are no longer coaxial. With this in mind, we return to our discussion of the cup-shaped flange 201 of the collar component 200.

In the exemplified embodiment, the cup-shaped flange 201 comprises four circumferentially spaced apart segments 201a-d located 90 degrees apart from one another. Each of the flange segments 201a-d comprises a fastener hole 204 through which one of the fasteners 15 extend when fixing the collar component to the socket 120. Of course, more or less than four flange segments could be implemented as desired. Furthermore, the cup-shaped flange 201 could also be a continuous (i.e., non-segmented) structure if desired. With respect to the lamination, the cup-shaped flange 201 acts as an anchoring structure for the collar component 200 in that is covered by the laminate 16 while the collar 205 protrudes through the laminate 16. The collar component 200 will be described in much greater detail with respect to FIGS. 2-6.

Referring again solely to FIG. 1, the prosthetic adapter 1000 also comprises a hub component 300 that is coupled to a prosthetic 10. This coupling can either be a direct coupling in which the hub component 300 is coupled directly to the prosthetic 10 without the existence of intervening parts (as illustrated in FIG. 1) or an indirect coupling in which one or more couplers, other adapters or intermediary members are disposed. Similarly, the coupling between the collar component 200 and the residual limb 20 can likewise be a direct or indirect coupling.

The hub component 300 generally comprises a hub 301, a body portion 302, and a male adapter block 303. In the exemplified embodiment, the male adapter block 303 is a pyramid block, the type of which is known in the art. The pyramid block 303 and the hub 301 are located on opposite ends (top and bottom) of the body portion 302. The hub component 300 is coupled, at one end, to the collar component 200 through mating of the hub 301 and the collar 205, and, at the other end, to the prosthetic 10 through mating of the pyramid block 303 and a pyramid block receiving cavity 9 of the prosthetic 10. The mating pyramid blocks with the pyramid block receiving cavities is known in the art and requires no further discussion. The mating of the hub 301 and the collar 205, however, will be described in much greater detail below with respect to FIGS. 7-9.

While the hub component 200 comprises a male connector block 303, in the form of a pyramid block, to couple to the prosthetic 10, the male connector block 303 may be replaced with a female receiving cavity in alternative embodiments, or with other types of male connecting blocks. In still further embodiments, the body portion 302 of the hub component 300 opposite the hub 301 can be adapted to be coupled to a prosthetic 10 via other structures and/or technique, now existing or later developed. For example, the body portion 302 can further comprise a clamp, a threaded fitting, a snap-fit mechanism, a tight-fit mechanism, twist-and-lock mechanism, a cotter pin mechanism, and/or combinations thereof.

Referring now to FIGS. 2-6 concurrently, the structural details of the collar component 200 and the hub component 300 will be described in greater deal. Turning first to the collar component 200, the collar component 200 comprises a collar 205 and a cup-shaped flange 201 as mentioned above. Preferably, the collar 205 and the cup-shaped flange 201 are integrally formed so as to be a unitary structure. In one preferred embodiment, the collar 205 and cup-shaped flange 201 are constructed of a metal (which includes metal alloys). Suitable metals may include without limitation steel and aluminum. Of course other metals and materials may be used, including plastics, ceramics, composite material, and/or combinations thereof. Additionally, in certain alternative embodiments, the collar 205 and cup-shaped flange 201 may be separate structures that are fixed together by welding, fastening or other techniques.

The collar 205 is a ring-like structure comprising an outer surface 207 and an inner surface 208. The inner surface 208 of the collar 200 forms a central cavity 209 about the first central axis I-I (FIG. 6) (which corresponds to the longitudinal axis A-A in FIGS. 2-5). The central cavity 209 is a cylindrical cavity having a circular transverse cross-sectional profile delimited by the inner surface 208. The circular transverse cross-sectional profile of the central cavity 209 (or though of another way the inner surface 208) has a first diameter $D_1$. The inner surface 208 forms an annular wall that circumferentially surrounds the first central axis I-I (FIG. 6) (which corresponds to the longitudinal axis A-A in FIGS. 2-5). A bottom edge 210 of the inner surface 208 is chamfered to help assist with guiding the hub 301 of the hub component 300 into the central cavity 209 during assembly of the collar and hub components 200, 300 together.

The collar 205 further comprises a plurality of threaded holes 211 extending transversely through the collar 205. The threaded holes 211 extend through the collar 205 from the outer surface 207 to the inner surface 208, thereby forming passageways from outside of the collar 205 to the central cavity 209. The inner surface of each of the threaded holes 211 comprises helical threads for threadliy engaging a set screw 212. The threaded holes 211 are arranged about the collar 205 in a circumferentially equi-spaced manner. In the exemplified embodiment, there are three threaded holes 211 arranged at 120 degree intervals about the collar 205. In alternative embodiments, more or less threaded holes 211 may be provided as desired, and in non-symmetric spacing arrangements.

A plurality of set screws 212 are also provided. A set screw 212 is positioned within each of the threaded holes 211 in a threadily engaged manner. The set screws 212 comprise a tip portion 213 and a head portion 214. The tip portion 213 has a tapered profile in the form of a truncated cone. The head portion 214 comprises an actuator so that a user can manually turn the set screw 212 by hand or with the use of a tool. In the exemplified embodiment, the actuator is in the form of hex cavity for receiving an appropriate bit or wrench. In alternative embodiments, the actuator can take on a wide variety of shapes and mechanisms, the number of which is too great to mention here but is well known to those skilled in the art.

As used herein, the term set screw is not limited to short cylinder screws as exemplified but is intended to include all types of bolts, screws, or other cylindrical bodies that can be translated along their axis through rotation about that axis. As will be discussed in greater detail below with respect to FIGS. 7-9, the set screws 212 are anti-rotation members that can be adjusted between different states to achieve different axial locking and anti-rotation effects on the hub 301 when the hub 301 is positioned within the central cavity 209.

The collar 205 further comprises a bottom surface 215 and a top 206. The cup-shaped flange 201 is located at and extends laterally outward from the top 206 of the collar 205. As mentioned above, the cup-shaped flange 201 forms a cup-shaped depression 203 for receiving the socket 120. The cup-shaped cavity 203 is in spatial cooperation/communication with the central cavity 209 so that a passageway is formed through the entire collar component 200 along the first central axis I-I (FIG. 6) (which corresponds to the longitudinal axis A-A in FIGS. 2-5).

Referring still to FIGS. 2-6 concurrently, we now turn to the hub component 200. Generally speaking, the hub component 200 is of the kind that is generally referred to in the industry as a shuttle lock design. The hub component 200 generally comprises a hub 301, a body portion 302, and a pyramid block 303. The body portion 302 comprises a top surface 304 and a bottom surface 305. The hub 301 extends from the top surface 304 along the second central axis II-II (FIG. 6) (which corresponds to the longitudinal axis A-A in FIGS. 2-5). The hub 301 is a cylindrical structure extending from the top surface 304 of the body portion 302. The hub 301 is centrally located on the body portion 302 and has a transverse cross-sectional profile at its base that is smaller than that of the body portion 302 at the top surface 304. As a result, the top surface 304 of the body portion 302 forms an annular shoulder that extends transversely outward from the hub 301 orthogonally to the second central axis II-II (FIG. 6) (which corresponds to the longitudinal axis A-A in FIGS. 2-5).

The hub 301 comprises an annular flange 306 extending from a lateral surface of the hub 301 that circumferentially surrounds the second central axis II-II (FIG. 6) (which corresponds to the longitudinal axis A-A in FIGS. 2-5). The annular flange 306 is located at the top of the hub 301 and is axially spaced apart from the top surface 304 of the body portion 302. The hub 301 further comprises an annular groove 308 formed into the lateral surface below the annular flange 306 that circumferentially surrounds the second central axis II-II (FIG. 6) (which corresponds to the longitudinal axis A-A in FIGS. 2-5). In the exemplified embodiment, the sidewalls of the annular grove 308 are formed by a bottom surface 309 of the annular flange 306 and the top surface 304 of the body portion 302. In alternative embodiments, however, the annular groove 308 may be formed as an isolated channel formed into the lateral surface of the hub 301 at a location where the channel's sidewalls will not be formed by the bottom surface 309 of the annular flange 306 or the top surface 304 of the body portion 302, but rather by surfaces created in the body of the hub 301 itself by the creation of the channel. Furthermore, while both the annular groove 308 and the annular flange 306 are preferably continuous and uninterrupted in nature, it may be possible to form these features as segmented structures or interrupted series of grooves or depressions.

The annular groove 308 comprises a floor 307. The floor 307 comprises a portion 307A that is inclined relative to the second central axis II-II (FIG. 6) (which corresponds to the longitudinal axis A-A in FIGS. 2-5). The portion 307A is preferably inclined relative to the second central axis II-II in an amount between 1° and 5°, and more preferably 2°. Of course, the invention is not to be so limited. In the exemplified embodiment, the inclined portion 307A has a transverse cross-sectional profile that tapers in size moving toward the body portion 302. In the preferred embodiment, the section of the hub 301 that forms the inclined portion 307A of the floor 307 of the annular groove 308 has a circular transverse cross-sectional profile that decreases in diameter moving toward the body portion 302. Thought of another way, the inclined portion 307A in this embodiment would form a truncated-cone shape that tapers to a smaller transverse cross-sectional area moving toward the body portion 302.

As discussed below, the inclined nature of the tapered portion 307A of the floor 307 of the annular groove 308 provides an improved connection between the collar component 200 and the hub component 300, and a substantial increase in the structural integrity when these components 200, 300 are assembled. In an alternative embodiment, the inclined portion 307A may have a contoured axial profile rather than a linear angled axial profile. Moreover, in other embodiments the inclined portion 307A may have other transverse cross-sectional profile shapes.

The floor 307 further comprises a section 307B that is parallel relative to the second central axis II-II (FIG. 6) (which corresponds to the longitudinal axis A-A in FIGS. 2-5). This parallel section 307B is located below the inclined section 307A. In other embodiments, the entire floor 307 may be inclined or parallel as desired.

The annular flange 306 has a circular transverse cross-sectional profile having a second diameter $D_2$. The second diameter $D_2$ is larger than the largest diameter of the transverse cross-sectional profile of the floor 307 of the annular groove 308. The hub 301 is also designed so that the second diameter $D_2$ is substantially equal to the first diameter $D_1$ of the transverse cross-sectional profile of the inner surface 208 of the collar 205. By making the second diameter $D_2$ substantially equal to the first diameter $D_1$, when the hub 301 is positioned within the central cavity 209 (as in FIGS. 2, 3 and 8), the first and second central axes I-I and II-II will be in coaxial alignment and the hub 301 will not be able to be rotated to move the first and second central axes I-I and II-II out of coaxial alignment without first removing the hub 301 from the central cavity 209. Thought of another way, by making the second diameter $D_2$ substantially equal to the first diameter $D_1$, when the hub 301 is positioned within the central cavity 209, the hub 301 has only two degrees of freedom, namely rotation about the first central axis I-I and translation along the first central axis I-I. Of course, as understood by those skilled in the art, a certain minimum tolerance between first diameter $D_1$ and the second diameter $D_2$ must be allotted to ensure that the hub 301 fits within the central cavity 308. The top edge 310 of the hub 301 is chamfered to assist with guiding the hub 301 into the central cavity 209 during assembly of the collar and hub components 200, 300.

Figure 6:
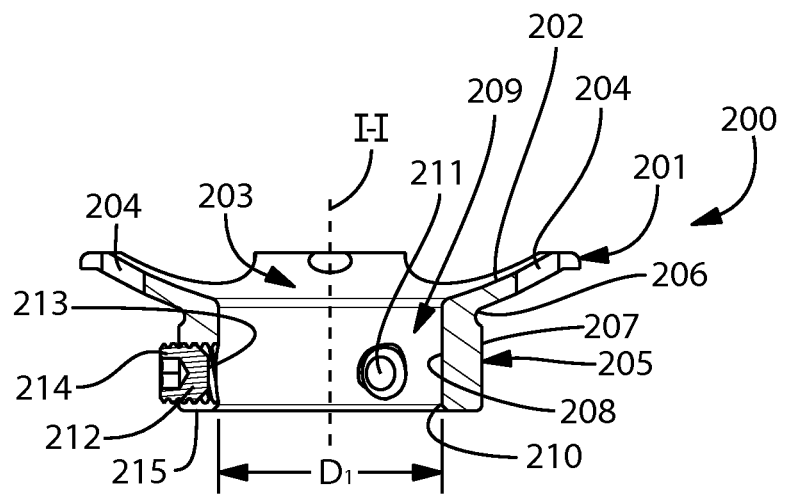
FIG. 6 is a vertical cross-sectional view of the collar component and shuttle lock component of FIG. 5 taken along the central axes.
Figure 6:
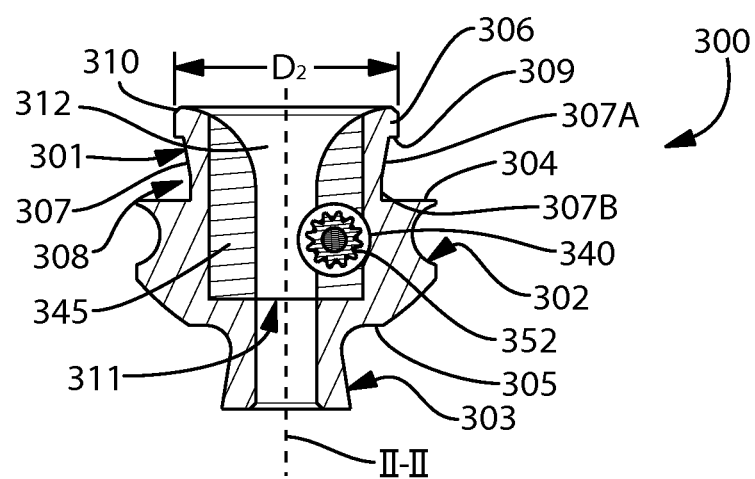

The hub component 300 further comprises an axial passageway 311 extending along the second central axis II-II (FIG. 6) (which corresponds to the longitudinal axis A-A in FIGS. 2-5). The axial passageway 311 forms a passageway through the hub 301, body portion 302, and pyramid block 303 of the hub component 300. The axial passageway 311 is provided to receive the clutch pin 115 of the sleeve assembly 100 when the hub component 300 is coupled to the collar component 200. The axial passageway 311 comprises a funnel shaped section 312 and a constant cross sectional area section 313 (FIG. 6).

The hub component 300 also comprises a clutch mechanism 350. The clutch mechanism comprises a helical reset spring 351, a locking gear 352, a one way bearing 353 (such as a sprag clutch), a push rod 354, and an actuator 355. The clutch mechanism 350 is slidably inserted into a transverse passageway 340 that extends from an outer surface of the body portion 302 to the axial passageway 311. The clutch mechanism 350 is slidably inserted into the transverse passageway 340 in the order of the reset spring 351, the locking gear 352, the one way bearing 353 and the push rod 354, which extends through the one way bearing 353. When the clutch mechanism 350 is assembled within the body portion 303, the spring 351 biases the locking gear 352 into a first position in which its teeth extend into the axial passageway 311. When the clutch pin 115 is inserted into the axial passageway 311, the serrated portion 117 of the clutch pin 115 is operably engaged by the locking gear 352. Because of the one way bearing 353, the clutch pin 115 can be translated only in a single direction along the second central axis II-II (FIG. 6) (which corresponds to the longitudinal axis A-A in FIGS. 2-5). When so assembled, the clutch mechanism 350 is actuatable (by pressing the actuator 355) between this first position in which the clutch pin 115 is engaged by the locking gear 352 and a second position in which the locking gear 352 is translated to disengage the clutch pin 115, thereby allowing the clutch pin 115 to be retracted from the axial passageway 311.

The body portion 302 further comprises a cleaning passageway 341 extending from the outer surface of the body portion to the transverse passageway 340 so that the internal components of the clutch mechanism 350 can be cleaned without the need for disassembly.

Preferably, the hub 301, the body portion 302 and the pyramid block 303 are integrally formed so as to be a unitary structure. In one preferred embodiment, the hub 301, body portion 302 and pyramid block 303 are constructed of a metal (which includes metal alloys). Suitable metals may include without limitation steel and aluminum. Of course other metals and materials may be used, including plastics, ceramics, composite material, and/or combinations thereof. Additionally, in certain alternative embodiments, the hub 301, the body portion 302 and the pyramid block 303 may be separate structures that are fixed together by welding, fastening or other techniques. Finally, a sheath 345 constructed of a different material than the hub 301, the body portion 302 and the pyramid block 303 may be disposed within body portion 302 to form the axial passageway 311. The sheath 345 can be formed of a plastic or other material that provides a reduced frictional surface for contact with the clutch pin 115 to reduce wear over time.

Figure 7:
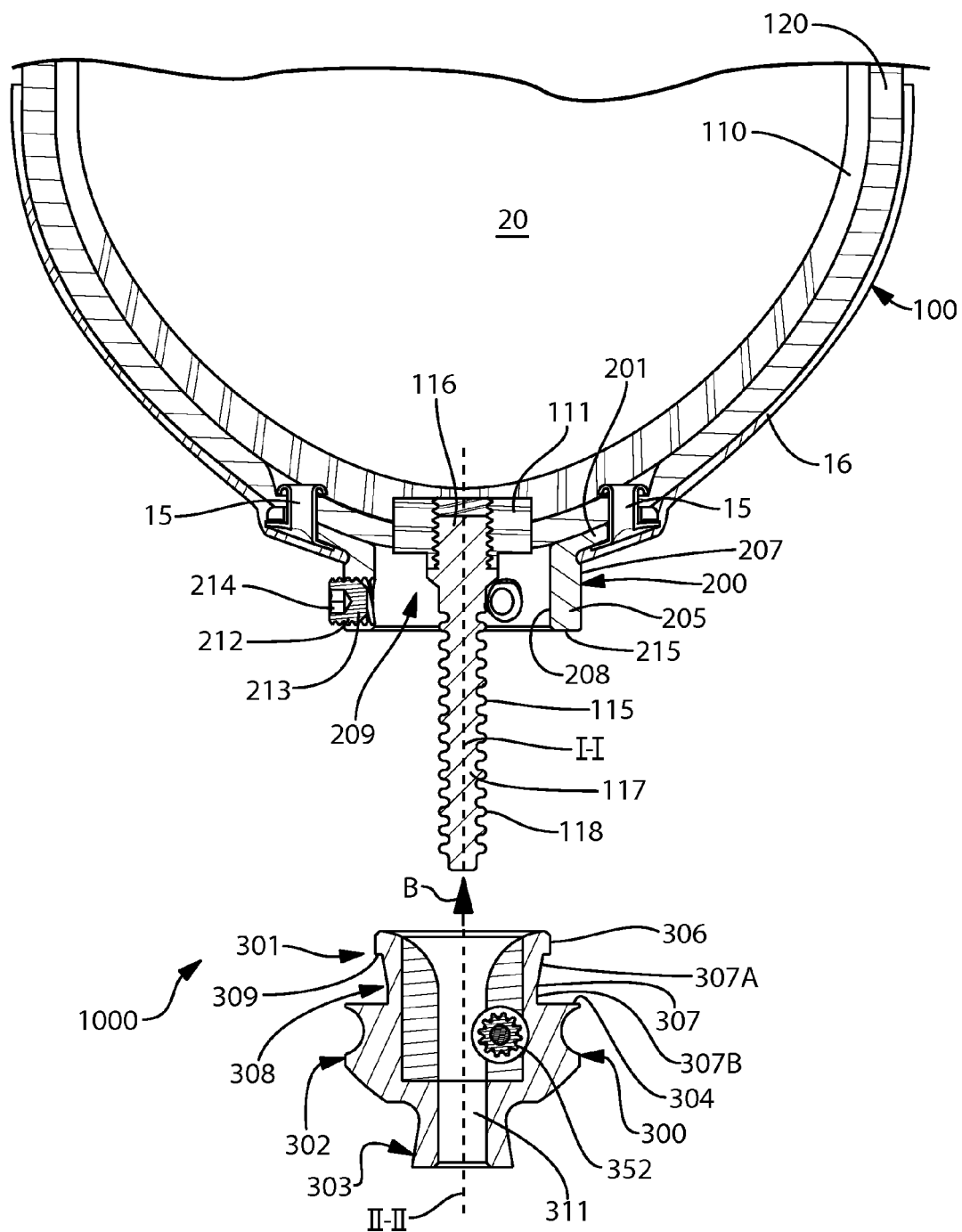
FIG. 7 is a cross-sectional schematic of the rotatable prosthetic adapter of FIG. 1 coupled to a residual limb, wherein the hub component is separated from the collar component.
Figure 8:
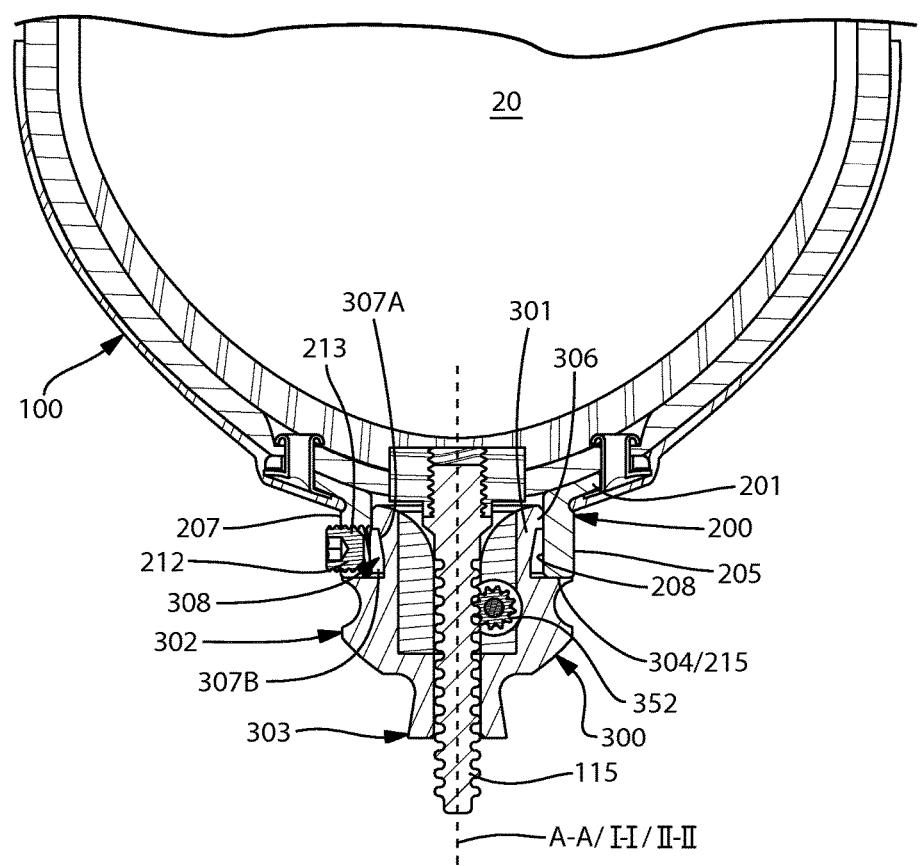
FIG. 8 is a cross-sectional schematic of the rotatable prosthetic adapter of FIG. 1 coupled to a residual limb wherein the hub component is mated with the collar component and the anti-rotation member is in a retracted state.
Figure 9:
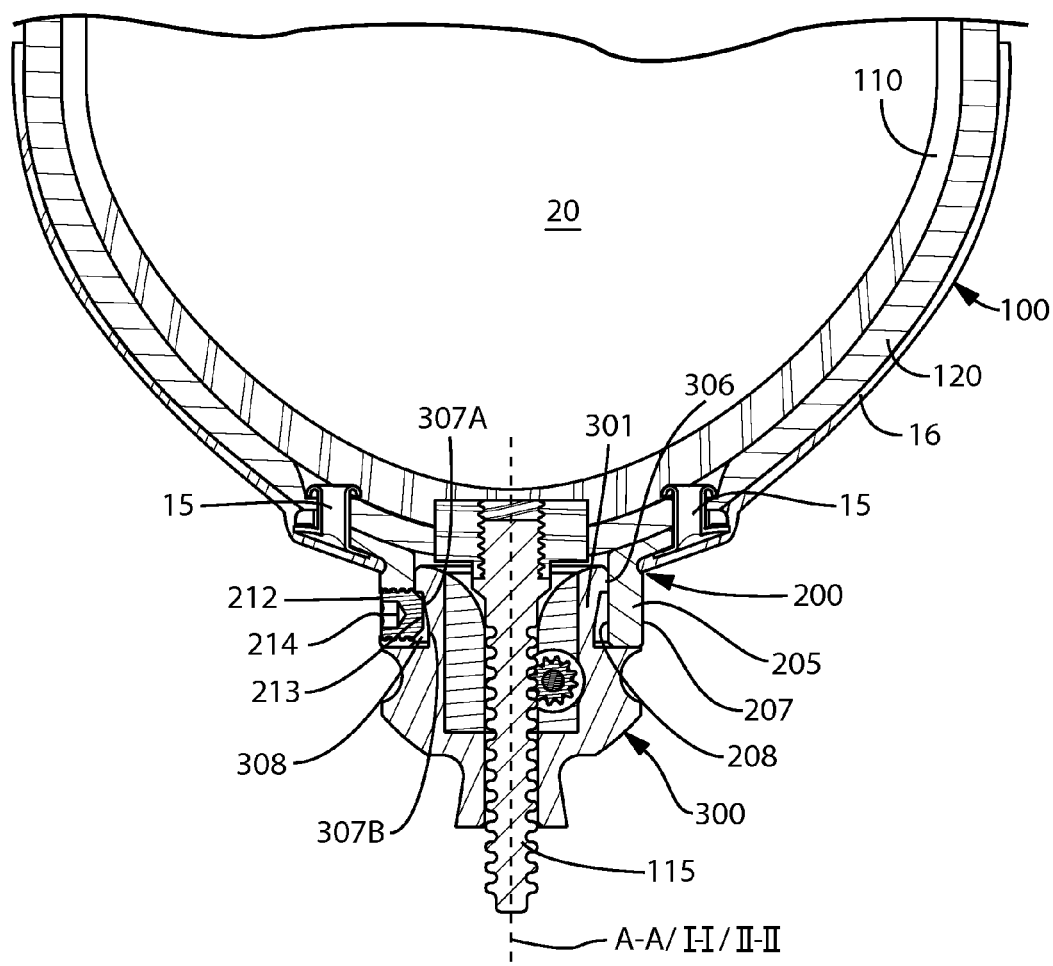
FIG. 9 is a cross-sectional schematic of the rotatable prosthetic adapter of FIG. 8, wherein the anti-rotation member has been adjusted to be in an anti-rotation state.
Figure 10:
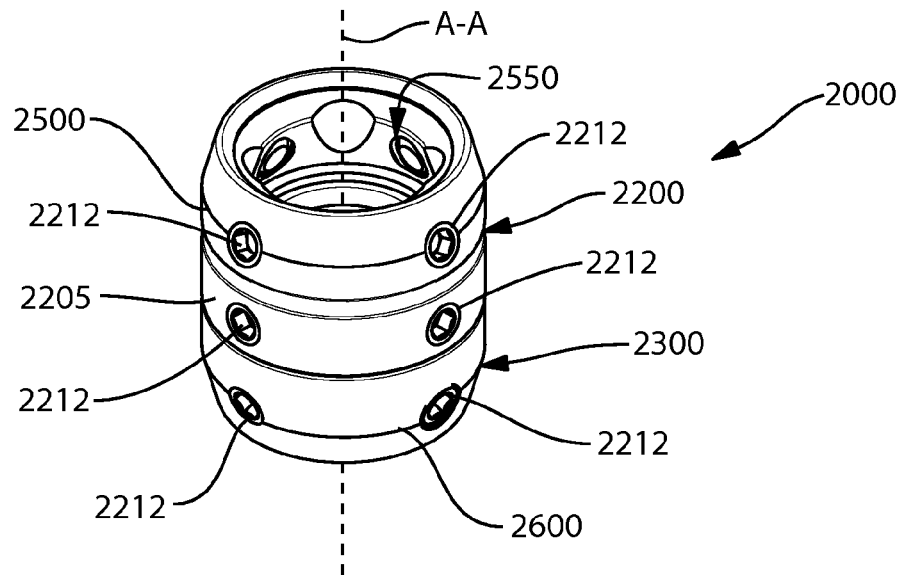
FIG. 10 is a top perspective view of a rotatable prosthetic adapter according to a second embodiment of the present invention.
Figure 11:
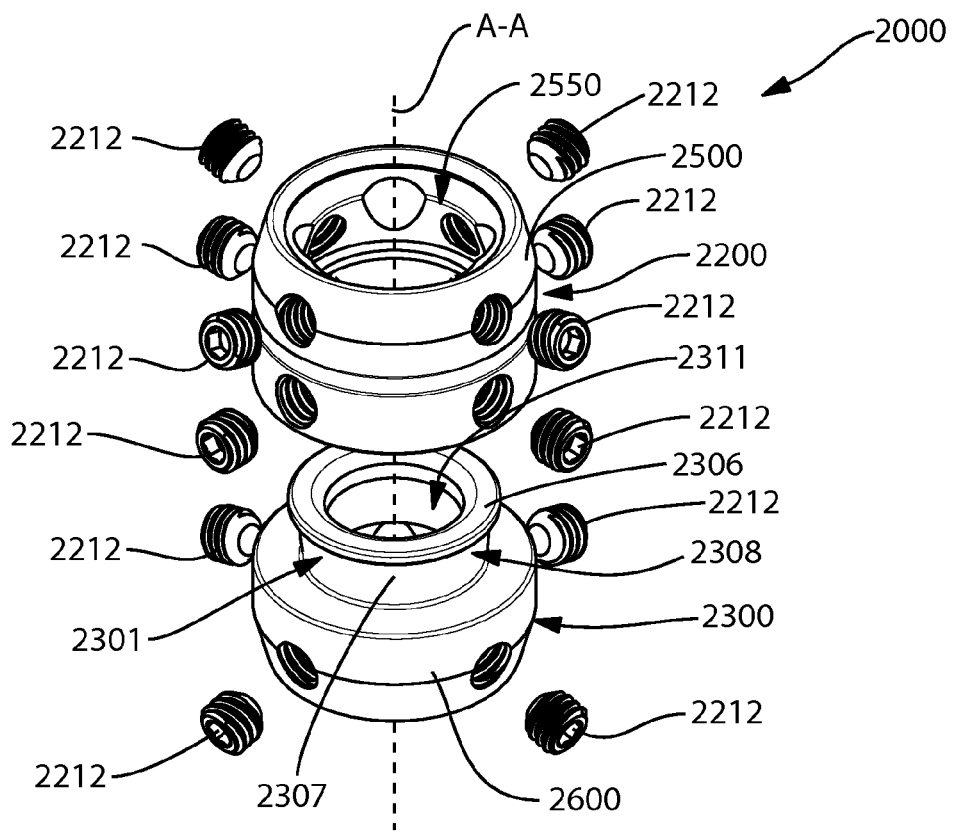
FIG. 11 is a top perspective view of the rotatable prosthetic adapter of FIG. 10 in an exploded state.
Figure 12:
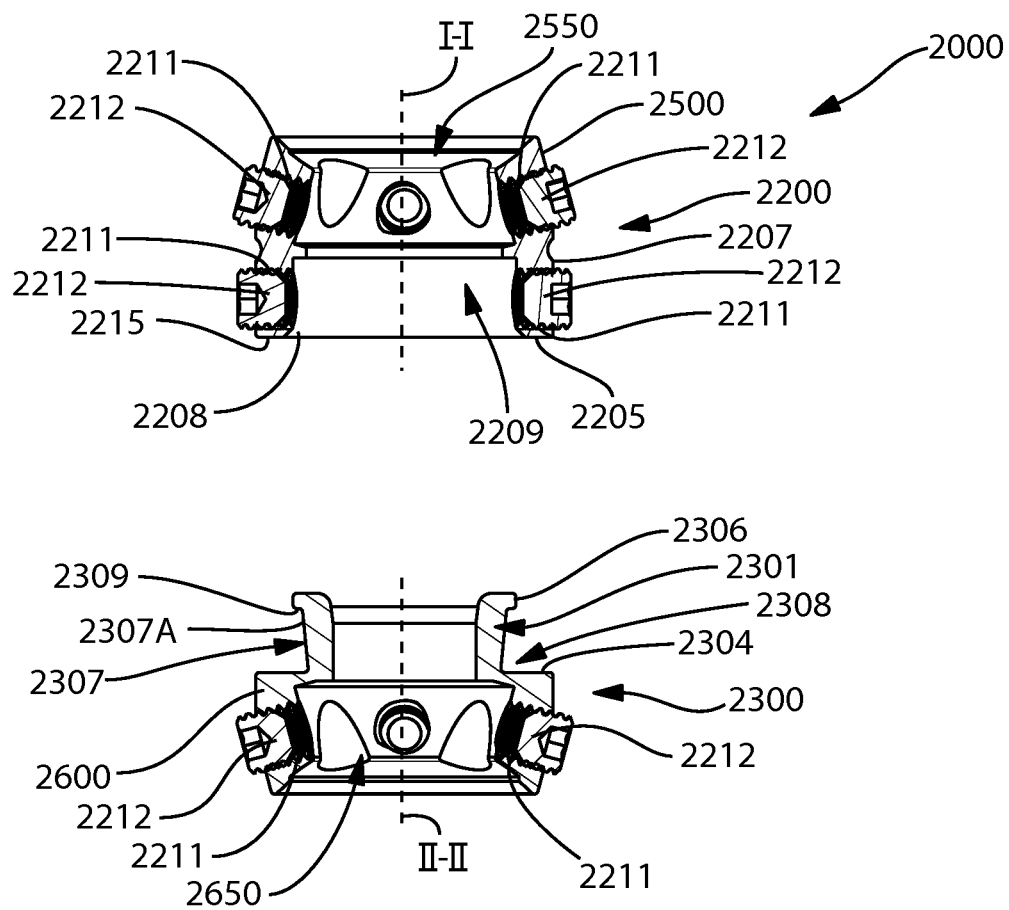
FIG. 12 is a cross-sectional view of the rotatable prosthetic adapter of FIG. 11 along the central axes.
Figure 13:
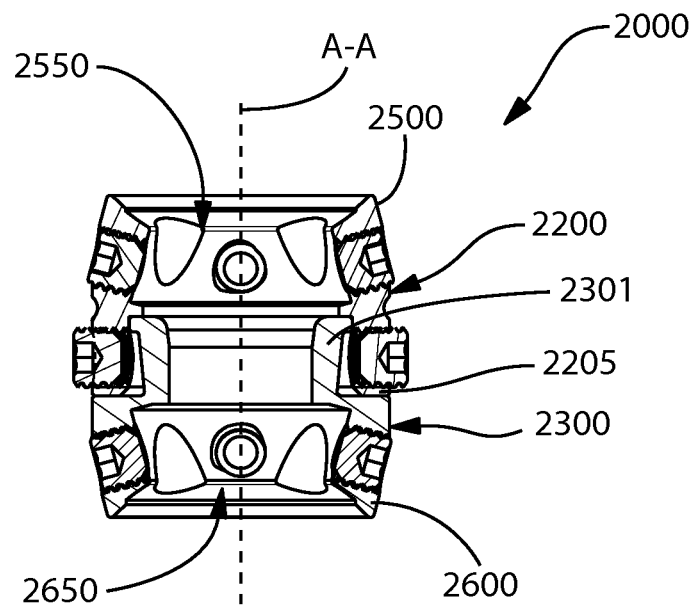
FIG. 13 is a cross-sectional view of the rotatable prosthetic adapter of FIG. 10 along the central axes wherein the hub component is mated with the collar component and the anti-rotation member is in a retracted state.
Figure 14:
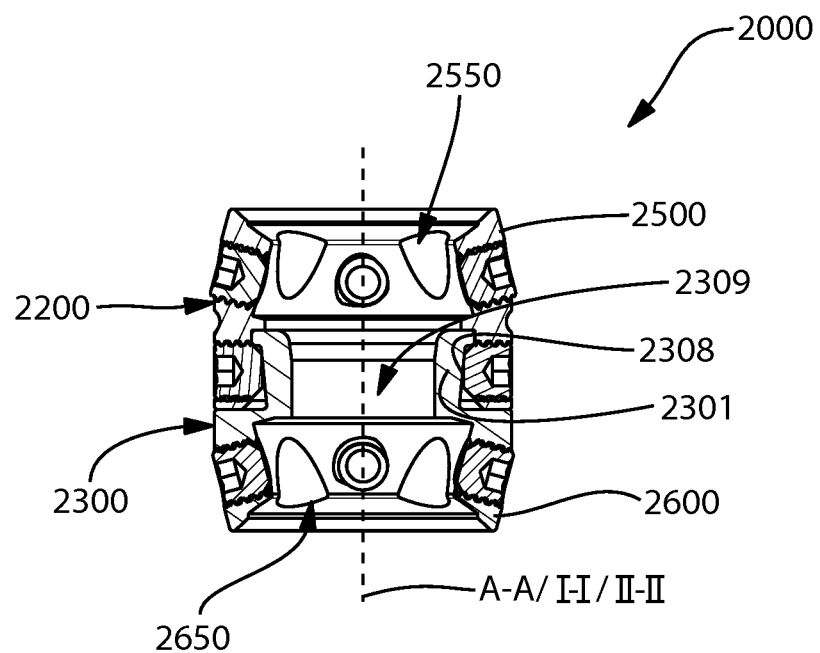
FIG. 14 is a cross-sectional schematic of the rotatable prosthetic adapter of FIG. 13 wherein the anti-rotation member has been adjusted to be in an anti-rotation state.

Referring now to FIGS. 7-9, the assembly of the collar component 200 and the hub component 300 of the rotatable prosthetic adapter 1000 will be discussed. Beginning with FIG. 7, when a user desires to use the rotatable prosthetic 1000, he/she first couples the collar component 200 to the residual limb 20 using the sleeve assembly 100 so that the clutch pin 115 extends along the first central axis I-I of the collar component 200, as discussed above with respect to FIG. 1. The user also couples the hub component 300 to the desired prosthesis 10 (omitted from FIGS. 7-9 for clarity) using the pyramid block 303, as also discussed above with respect to FIG. 1. If necessary, the set screws 212 are adjusted to ensure that the set screws 212 are in a retracted state in which the tip portions 213 of the set screws 212 do not protrude from the inner surface 208 of the collar 205 (i.e., into the central cavity 209). When in the retracted state, the set screws 212 do not interfere with or obstruct the hub 201 from being fully inserted fully into (or removed from) the central cavity 209 of the collar 205.

Once this is done, the hub component 200 is aligned with the collar component 300 so that first and second central axes I-I and II-II are substantially coaxial. The hub component 200 is then translated in a direction along the second central axis II-II, indicated by arrow B.

The translation of the hub component 200 along the second central axis II-II is continued until the hub 301 slides into the central cavity 209 of the collar 205 so that the bottom surface 215 of the collar 205 of the collar component 200 is in surface contact with the top surface 304 of the body portion 303 of the hub component 200, thereby forming an interface therebetween. Concurrently during this translation, the clutch pin 115 also slides into axial passageway 311 of the hub component 300, thereby engaging the locking gear 352 as discussed above. At this stage, the hub 302 is positioned within the central cavity of the collar 205, and the clutch pin 115 is positioned within the axial passageway 311, as illustrated in FIG. 8.

Referring now to FIG. 8, the hub component 200 is assembled to the collar component 300 by the positioning of the hub 302 within the central cavity 209 of the collar 205.

However, the set screws 212 remain in their retracted state. As mentioned above, even in this arrangement, because the transverse cross-sectional profiles of the inner surface 208 of the collar 205 and the annular flange 306 have substantially the same diameter, the first and second central axes I-I and II-II are forced into coaxial alignment and the hub 301 can not be rotated to move the first and second central axes I-I and II-II out of coaxial alignment without first removing the hub 301 from the central cavity 209. Thought of another way, as illustrated in FIG. 8, the hub 301 has only two degrees of freedom, namely rotation about the first central axis I-I and translation along the first central axis I-I out of the central cavity 209. As can be seen, at this stage, the annular flange 306 is located above the set screws 212 (and threaded holes 211) and the annular groove 308 is in transverse alignment with the set screws 212 (and threaded holes 211).

Once the relative positioning of FIG. 8 is achieved, the user adjusts the set screws 212 from the retracted state into an anti-rotation state in which the tip portions 213 of the set screws 212 protrude from the inner surface 208 of the collar 205, move into the annular groove 308 of the hub 301, and engage the inclined portion 307A of the floor 307 of the annular groove 308. This arrangement is illustrated in FIG. 9.

Referring now to FIG. 9, when the set screws 212 are in the anti-rotation state, the hub 301 is prohibited from rotating about the first central axis I-I within the central cavity 209 of the collar 205. Additionally, the contact between the tip portions 213 of the set screws 212 and the inclined portions 307A of the floor 307 of the annular groove 308 urges the hub component 300 and the collar component 200 together, thereby providing an improved connection and rigidity between the two components 200, 300. The inclined nature of the floor portion 307A results in the set screws 212 generating an axial force on the hub component 300 as the set screws are tightened, thereby further forcing the hub component 300 and the collar component 200 to pull closer together. As a result, the engagement between the hub component 300 and the collar component 200 becomes stronger and relative rotation between the two components 200, 300 is prohibited.

While not illustrated, it is important to understand that in the event the prosthesis 10 were to be undesirably rotated about the longitudinal axis A-A during use, the prosthetic adapter 1000 of the present invention allows for a quick and discreet rotational adjustment of the prosthesis 10 without the danger of the prosthesis 10 becoming completely separated from the residual limb 20. This is accomplished by adjusting the set screws 212 to an intermediate state between the retracted state and the anti-rotation state in which the tip portions 213 of the set screws 212 extend into the annular groove 308 of the hub 301 but do not engage the floor 307. In this state, referred to as the axial locking state, the hub 301 can rotate about the first central axis I-I but is prohibited from translating along the first central axis I-I out of the central cavity 209 due to contact between the tip portions 213 of the set screws 212 and the annular flange 306.

Referring now to FIGS. 10-14 concurrently, a rotatable prosthetic adapter 2000 according to a second embodiment of the present invention is illustrated. The rotatable prosthetic adapter 2000 of FIGS. 10-14 is identical to the rotatable prosthetic adapter 1000 of FIGS. 1-9 with the exception that: (1) the collar component 2200 comprises a pyramid block receiver 2500 rather than an annular flange; and (2) the hub component 2300 comprises a pyramid block receiver 2600 as its body portion rather than a shuttle-lock. Thus in order to avoid redundancy, only those aspects of the rotatable prosthetic adapter 2000 that are different than the rotatable prosthetic adapter 1000 of FIGS. 1-9 will be discussed herein with the understanding that the aforementioned discussion of FIGS. 1-9 is applicable. Moreover, in FIGS. 10-14, like numbers are used to identify like elements with the exception that the numbers are in the "2000" series. For example, "the tapered portion 307A of the floor 307 of the annular groove 308" from FIGS. 1-9 corresponds to "the tapered portion 2307A of the floor 2307 of the annular groove 2308" from FIGS. 10-14.

The rotatable prosthetic adapter 2000 comprises a collar component 2200 and a hub component 2300. The collar component 2200 is a tubular structure comprising a pyramid block receiver 2500 and a collar 2205. The pyramid block receiver 2500 forms an upper portion of the collar component 2200 while the collar 2205 forms a lower portion of the collar component 2200. The pyramid block receiver 2500 extends from a top of the collar 2205 and is integrally formed therewith. The pyramid block receiver 2500 is an annular and slight conical structure comprising a pyramid block receiving cavity 2550 that is sized and shaped to receive a male pyramid block. The pyramid block receiving cavity 2550 is in spatial communication with the central cavity 2209 of the collar 2205. The pyramid block receiver 2500 comprises a plurality of threaded holes 2211 arranged in spaced apart manner and aligned at a non-normal angle relative to the first central axis I-I. Set screws 212 threadliy engage the threaded holes 2211 of the pyramid block receiving cavity 2550.

The hub component 2300 is a tubular structure comprising a hub 2301 and a pyramid block receiver 2600. The hub 2301 forms an upper portion of the hub component 2300 while the pyramid block receiver 2600 forms a lower portion of the hub component 2300. The hub 2301 extends from a top surface 2304 of the pyramid block receiver 2600 and is integrally formed therewith. The pyramid block receiver 2600 is an annular and slight conical structure comprising a pyramid block receiving cavity 2650 that is sized and shaped to receive a male pyramid block. The pyramid block receiving cavity 2650 is in spatial communication with a passageway 2311 of the hub 2301. The pyramid block receiver 2600 comprises a plurality of threaded holes 2211 arranged in spaced apart manner and aligned at a non-normal angle relative to the first central axis I-I. Set screws 2212 threadily engage the threaded holes 2211 of the pyramid block receiving cavity 2550.

The floor 2307 of the hub 2301 is formed only of an inclined portion 2307A that is preferably angled between 1° and 5° relative to the axis II-II, and more preferably 2° relative to the axis II-II. Of course, the invention is not so limited and the floor 2307 of the hub 2301 may have an inclined portion and a portion that is parallel to the axis II-II as described above.

The hub 2301 of the hub component 2300 mates with the central cavity 2209 of the collar 2205 of the collar component 2200 in the exact same manner as that set forth above with respect to FIGS. 1-9. Additionally, while both of the hub component 2300 and the collar component 2200 comprise a pyramid block receiver, either or both of these pyramid block receivers can be replaced by a male pyramid block or another type of coupling or linking structure as desired. It should become apparent from the discussion set forth herein that the hub and collar coupling concept of the present invention can be used with almost any other structure.

Finally, in the embodiments of the rotatable prosthetic adapters 1000, 2000 illustrated in FIGS. 1-14, set screws are the exemplified anti-rotation member that is adjustable to achieve the desired retracted, axial-locking, and anti-rotation states. The invention, however, is not limited to the use of set screws as the anti-rotation member. In other embodiments, the anti-rotation member may take the form of one or more spring-loaded cylindrical pins that extend through the collar. In such an embodiment, the spring-loaded cylindrical pins may be biased into the anti-rotations state and have a locking mechanism for holding the spring-loaded cylindrical pins in the retracted state during assembly. Additionally, in another embodiment, a clamp can be used to either adjust the engagement force imparted by the collar on the hub and/or to extend and retract protrusions into and out of the central cavity through adjustment of the clamp. Furthermore, while the anti-rotation member is preferably in the form of cylindrical element, such as a screw or pin, it is to be understood that the anti-rotation member can take on a wide variety of structures, including arcuate members, block-like members, or any protuberance.

While a number of embodiments of the current invention have been described and illustrated in detail, various alternatives and modifications will become readily apparent to those skilled in the art without departing from the spirit and scope of the invention. As various changes could be made in the above methods, compositions and structures without departing from the scope of the invention, it is intended that all matter contained in this application, including all mechanisms and/or modes of interaction described above, shall be interpreted as illustrative only and not limiting in any way the scope of the appended claims.

What is claimed is:

1. A prosthetic adapter comprising:
   a first component comprising:
      a first pyramid block receiver comprising a first pyramid block receiving cavity;
      a collar integrally formed as a single monolithic component with the first pyramid block receiver, the collar comprising an inner surface forming a central cavity formed about a first central axis;
   a second component comprising:
      a second pyramid block receiver comprising a second pyramid block receiving cavity; and
      a hub integrally formed as a single monolithic component with the second pyramid block receiver, the hub comprising a flange and a groove comprising a floor, the hub extending along a second central axis, the hub positioned in the central cavity so that the first and second central axes are coaxial;
   wherein when the hub is positioned within the central cavity of the collar with a bottom surface of the collar in surface contact with a top surface of the second pyramid block receiver, the hub has only two degrees of freedom, a first of the two degrees of freedom being rotation about the first central axis, and a second of the two degrees of freedom being slidable translation along the first central axis; and
   an anti-rotation member mounted to the collar, the anti-rotation member adjustable to an anti-rotation state in which a tip portion of the anti-rotation member engages the floor of the groove and rotation of the hub relative to the collar is prohibited.

2. The prosthetic adapter of claim 1 wherein the bottom surface of the collar is perpendicular to the first central axis and the top surface of the second pyramid block receiver is perpendicular to the second central axis, the top surface of the pyramid block receiver forming a shoulder that extends transversely outward from the hub.

3. The prosthetic adapter of claim 1 wherein the hub comprises:
   the flange comprising a sidewall surface that is parallel to the second central axis and a bottom surface that is perpendicular to the second central axis;
   wherein at least a portion of the floor of the groove is inclined relative to the second central axis;
   the inclined portion of the floor of the groove intersecting and extending from the bottom surface of the flange toward the top surface of the second pyramid block receiver; and
   wherein when the anti-rotation member is in the anti-rotation state, the tip portion of the anti-rotation member engages the inclined portion of the floor of the groove, thereby urging the first and second components together.

4. The prosthetic adapter of claim 1 wherein the collar has a fixed diameter.

5. The prosthetic adaptor of claim 1 wherein the floor of the groove is located between the flange and the top surface of the second pyramid block receiver.

6. A prosthetic adapter comprising:
   a first component comprising:
      a first pyramid block receiver comprising a first pyramid block receiving cavity; and
      a collar integrally formed as a single monolithic component with the first pyramid block receiver, the collar extending from the first pyramid block receiver, the collar having an inner surface forming a central cavity about a first central axis;
   a second component comprising:
      a second pyramid block receiver comprising a second pyramid block receiving cavity; and
      a hub integrally formed as a single monolithic component with the second pyramid block receiver, the hub extending from the second pyramid block receiver along a second central axis, the hub comprising a flange spaced from the second pyramid block receiver so that a groove is formed between a top surface of the second pyramid block receiver and a bottom surface of the flange; and
   an anti-rotation member mounted to the collar, wherein when the hub of the second component is positioned in the central cavity of the collar of the first component, the anti-rotation member is adjustable between: (1) a first state in which the anti-rotation member does not obstruct the hub from being translated along the first central axis out of the central cavity; (2) a second state in which the anti-rotation member prohibits the cylindrical hub from being translated along the first central axis out of the central cavity while allowing the hub to rotate within the central cavity of the collar about the first central axis; and (3) a third state in which the anti-rotation member prohibits the hub from being translated along the first central axis out of the central cavity of the collar and prohibits rotation of the hub within the central cavity of the collar about the first central axis.

7. The prosthetic adapter of claim 6 wherein a portion of the inner surface of the collar is parallel to the first central axis; and wherein the hub is positioned in the central cavity and maintained, by contact between a sidewall surface of the flange and the portion of the inner surface of the collar, so that the first and second central axes are in coaxial alignment, wherein the sidewall surface of the flange is parallel to the second central axis and the bottom surface of the flange is perpendicular to the second central axis.

8. The prosthetic adapter of claim 6 further comprising:
the collar comprising a threaded hole extending through the collar from an outer surface of the collar to the inner surface of the collar;
the anti-rotation member threadily engaged within the threaded hole; and
wherein, in the first state, the anti-rotation member does not protrude from the inner surface of the collar, and, in the second state, a tip portion of the anti-rotation member extends into the groove but does not contact a floor of the groove, and, in the third state, the tip portion of the anti-rotation member engages the floor of the groove.

9. The prosthetic adapter of claim 8 further comprising: at least a portion of the floor of the groove being inclined relative to the second central axis; the inclined portion of the floor of the groove extending from the bottom surface of the flange and having a circular transverse cross-sectional profile that tapers in size moving toward the second pyramid block receiver; and wherein, in the third state, the tip portion of the anti-rotation member engages the inclined portion of the floor of the groove, thereby urging the first and second components together.

10. The prosthetic adapter of claim 6 wherein the second pyramid block receiver of the second component comprises a shoulder extending outwardly from the cylindrical hub, and wherein when the cylindrical hub is positioned in the central cavity, surface contact between the shoulder and a first end of the collar prohibits the cylindrical hub from protruding beyond a second end of the collar that is opposite the first end.

11. The prosthetic adapter of claim 6 wherein when the anti-rotation member is in the first state, the hub cannot be pivoted to move the first and second central axes out of said coaxial alignment.

12. The prosthetic adapter of claim 6 wherein the collar of the first component comprises a bottom surface, the hub extending from a top surface of the second pyramid block receiver, and wherein when the hub is fully inserted within the central cavity the bottom surface of the collar and the top surface of the second pyramid block receiver are in contact with one another.

13. The prosthetic adapter of claim 6 wherein the flange of the hub is an annular flange circumferentially surrounding the second central axis, the annular flange having a circular transverse cross-sectional profile having a first diameter; the inner surface of the collar having a circular transverse cross-sectional profile having a second diameter; and wherein the first and second diameters are equal.

14. A prosthetic adapter comprising:
a first component comprising an upper portion and a lower portion, the upper portion of the first component comprising a first pyramid block receiver comprising a first pyramid block receiving cavity, the lower portion of the first component comprising a collar having an outer surface and an inner surface, the inner surface forming a central cavity about a first central axis, the first pyramid block receiver extending from a top of the collar and monolithically formed therewith;
a second component comprising an upper portion and a lower portion, the lower portion of the second component comprising a second pyramid block receiver comprising a second pyramid block receiving cavity, the upper portion of the second component comprising a cylindrical hub extending from the second pyramid receiver along a second central axis and monolithically formed therewith, the cylindrical hub positioned in the central cavity so that the first and second central axes are coaxial;
wherein when the cylindrical hub is positioned within the central cavity of the collar, the hub has only two degrees of freedom, a first of the two degrees of freedom being rotation about the first central axis, and a second of the two degrees of freedom being translation along the first central axis; and
an anti-rotation member adjustable between: (1) a first state in which the anti-rotation member does not obstruct the cylindrical hub from being translated along the first central axis out of the central cavity; (2) a second state in which the anti-rotation member prohibits the cylindrical hub from being translated along the first central axis out of the central cavity while allowing the cylindrical hub to rotate within the central cavity of the collar about the first central axis; and (3) a third state in which the anti-rotation member prohibits the cylindrical hub from being translated along the first central axis out of the central cavity of the collar and prohibits rotation of the cylindrical hub within the central cavity of the collar about the first central axis.

15. The prosthetic adapter of claim 14 further comprising:
the cylindrical hub comprising: an annular groove circumferentially surrounding the second central axis; and an annular flange circumferentially surrounding the second central axis, the annular groove located between the annular flange and the second pyramid receiver; and
the anti-rotation member comprising at least one cylindrical element that extends through a hole extending from the outer surface of the collar to the inner surface of the collar; and
wherein, in the first state, the cylindrical element does not protrude from the inner surface of the collar, and, in the second state, a tip portion of the cylindrical element extends into the annular groove but does not contact a floor of the annular groove, and, in the third state, the tip portion of the cylindrical element engages the floor of the annular groove.

16. The prosthetic adapter of claim 15 further comprising:
at least a portion of the floor of the annular groove being inclined relative to the second central axis;
the inclined portion having a circular transverse cross-sectional profile that tapers in size moving toward the second pyramid receiver; and
wherein, in the third state, the tip portion of the of the cylindrical element engages the inclined portion of the floor of the annular groove, thereby urging the first and second components together.

17. The prosthetic adapter of claim 16 wherein the cylindrical element is a set screw and the hole is threaded, the set screw in threaded cooperation within the threaded hole.

18. The prosthetic adapter of claim 14 further comprising:
wherein when the anti-rotation member is in the first state, the cylindrical hub cannot be pivoted to move the first and second central axes out of coaxial alignment without translating the cylindrical hub at least partially out of the central cavity of the collar.

19. The prosthetic adapter of claim 14 wherein the collar comprises a bottom surface and the second pyramid receiver comprises a top surface, the cylindrical hub extending from the top surface of the second pyramid receiver, and wherein the bottom surface of the collar and the top surface of the second pyramid receiver are in contact with one another so as to form an interface extending transversely to the first and second axes.

20. The prosthetic adapter of claim 14 wherein the cylindrical hub comprises:
- an annular flange circumferentially surrounding the second central axis, the annular flange having a circular transverse cross-sectional profile having a first diameter;
- the inner surface of the collar having a circular transverse cross-sectional profile having a second diameter; and
- wherein the first and second diameters are equal.

* * * * *